United States Patent
Tarletsky et al.

(10) Patent No.: US 6,630,151 B1
(45) Date of Patent: Oct. 7, 2003

(54) METHOD OF INCREASING VISCOSITY OF OIL-BASED COMPOSITIONS AND COMPOSITIONS RESULTING THEREFROM

(75) Inventors: Christopher J. Tarletsky, Bloomsbury, NJ (US); Richard J. Nadolsky, Tulsa, OK (US); Shawn L. Myers, Broken Arrow, OK (US)

(73) Assignee: Baker Hughes Incorporated, Houston, TX (US)

( * ) Notice: Subject to any disclaimer, the term of this patent is extended or adjusted under 35 U.S.C. 154(b) by 886 days.

(21) Appl. No.: 08/864,009

(22) Filed: May 27, 1997

(51) Int. Cl.⁷ .................................................. A61K 6/00
(52) U.S. Cl. .................. 424/401; 424/70.12; 424/78.03
(58) Field of Search ............................ 424/401, 59, 65, 424/70.12, 78.03; 514/506, 557, 558, 844, 845, 846, 847, 848, 944

(56) References Cited

U.S. PATENT DOCUMENTS

| | | | |
|---|---|---|---|
| 4,569,784 A | 2/1986 | Moore | 252/315.1 |
| 4,605,563 A | 8/1986 | Heine et al. | 426/607 |
| 4,643,850 A | 2/1987 | Hülsmann et al. | 260/410.7 |
| 4,699,924 A | 10/1987 | Durrant et al. | 514/558 |
| 4,791,140 A | 12/1988 | Fukasawa et al. | 514/845 |
| 5,124,361 A | 6/1992 | Fukasawa et al. | 514/772 |
| 5,169,967 A | 12/1992 | Assmus | 554/71 |
| 5,171,577 A | 12/1992 | Griant | 424/450 |
| 5,260,055 A * | 11/1993 | Imperante et al. | 424/71 |
| 5,288,482 A * | 2/1994 | Krzysik | 424/64 |
| 5,902,570 A * | 5/1999 | Bretzler | 424/65 |
| 6,235,824 B1 * | 5/2001 | Vander Louw et al. | 524/278 |

OTHER PUBLICATIONS

Petrolite Corp., UNICID, Trademark, p. 1, 1992.*

* cited by examiner

Primary Examiner—Jose' G. Dees
Assistant Examiner—Michael A. Williamson
(74) Attorney, Agent, or Firm—Locke Liddell & Sapp LLP (57) ABSTRACT

A process of preparing a composition of enhanced viscosity comprises adding to a liquid oil, a high molecular weight solid monocarboxylic acid having a number average molecular weight of less than 3,000. The resulting composition is considerably more viscous than the compositions of the prior art and has particular applicability in the cosmetic and pharmaceutical industries.

46 Claims, 4 Drawing Sheets

METHOD OF INCREASING VISCOSITY OF OIL-BASED COMPOSITIONS AND COMPOSITIONS RESULTING THEREFROM

FIELD OF THE INVENTION

The invention relates to a method of increasing the viscosity of a composition containing an oil by the addition of a long chain carboxylic acid. In addition, the invention relates to the resultant composition. In particular, the invention relates to a process of thickening oils, thereby enhancing the viscosity of desired formulations. The invention has particular applicability in the cosmetic and pharmaceutical industries.

BACKGROUND OF THE INVENTION

A large number of lubricant formulations are used in various technical fields, especially in the cosmetic and pharmaceutical industries. The viscosity of such formulations is increased by using various oil thickening agents. In the cosmetic industry, the resulting products are often referred to as oleogels. In the pharmaceutical industry, such products are often referred to as pharmaceutical adjuvants.

Typically, highly dispersed silica including clays, fumed silicas, castor wax and microcrystalline high-melting fats such as hardened glycerides of relatively long chain length, have been used to increase the viscosity of lubricant formulations. In light of their thickening capabilities, metallic soaps, fatty acid dextrin esters, metallic salts of dialkyl phosphate and organic-denatured bentonites have further been used as thickening agents for medicines and cosmetics. Most particularly, the prior art tended to favor the use of hydrogenated castor oil.

The thickening systems of the prior art were relatively unstable at elevated temperatures. When stored or transported under higher temperature conditions, such systems often decomposed. In addition, such systems often were highly filamentous.

Organic-denatured bentonites have further been used as thickening agents for providing thixotropic rheological characteristics to oils. Organic-denatured bentonites, however, are generally produced through intercalation of an alkyl amine on montmorillonite which is a clay mineral. This poses a problem in view of safety of alkyl amine when the material is used for medicines or cosmetics. Furthermore, the turbidity caused by an organic-denatured bentonite, in light of inclusions of montmorillonite, often affected the color of the resulting composition. For this reason, organic-denatured bentonites are unsuitable in those circumstances where the resultant composition is to have a delicate color tone.

There is, therefore, a strong need for the development of thickening agents having thixotropic and rheologically acceptable characteristics, which exhibit good color while imparting a fresh feel to the users, which does not form filamentous materials and which is heat stable.

SUMMARY OF THE INVENTION

The invention relates to a process of preparing a composition of enhanced viscosity and a composition resulting therefrom. The process consists of adding to an oil a monocarboxylic acid having a number average molecular weight of less than 3,000.

The amount of carboxylic acid used in combination with the oil is between from about 1.0 to about 20% by weight.

The resulting composition exhibits good heat stability, is non-filamentous and is a desired feel modifier. Such compositions may be used topically or internally and have particular utility in the production of cosmetics and pharmaceuticals.

The carboxylic acids employed in the invention are preferably a monocarboxylic acid of the formula RCOOH wherein R is a branched or linear saturated hydrocarbon chain of number average molecular weight less than 3,000.

DETAILED DESCRIPTION OF THE INVENTION

The invention is directed to a method of thickening oils, thereby increasing the viscosity of the resulting compositions. In addition, the invention is directed to the resulting compositions. Such compositions demonstrate improvements in viscosity and heat stability over the formulations of the prior art. Such compositions may be a solid or liquid. By "liquid" it is meant a composition which is either pourable, gelled or gel-like as exhibits the consistency of a paste, cream or ointment. The invention has particular applicability in the production of gels (including lipsticks and deodorants) and creams (such as sunscreen, cold cream and shaving cream).

The invention encompasses the addition of a rheologically effective amount of solid monocarboxylic acid to an oil in order to increase the viscosity of the oil. The composition exhibits a viscosity highly desirable in the cosmetic industry as well as in the pharmaceutical industry.

The high molecular weight carboxylic acid for use in the invention typically may be represented by the formula RCOOH wherein R is a branched chain or branched saturated hydrocarbyl radical. The number average molecular weight of the solid carboxylic acid is generally less than 3,000 and greater than 300. Carboxylic acids with a molecular weight higher than 3,000 typically do not render smooth dispersions. Carboxylic acids having a molecular weight of less than about 300 do not adequately effectuate an increase in the viscosity of the composition. In a preferred embodiment, the molecular weight of the long chain carboxylic acid is between about 300 and about 2,000. In the more preferred embodiment, the molecular weight of the long chain carboxylic acid is between 300 and about 800. (As used throughout the specification, unless otherwise noted, the term "molecular weight" refers to number average molecular weight.)

The long chain monocarboxylic acids of the invention may be prepared by several methods. One of these consists of oxidizing the alcohol represented by the formula:

wherein R and $R_1$ independently represent hydrogen or a lower alkyl group of from 1 to about 10 carbon atoms and x represents a number of from about 8 to about 142, preferably from about 8 to about 112, most preferably from about 10 to about 24. Oxidation reagents and processes for effectuating the production of such carboxylic acids are well known in the art. Included within this group are those commercially available from Petrolite Polymers Division under the trademark UNILIN® alcohols or from New Phase Technologies under the trademark PERFORMACOL® alcohols. Such alcohols are derived by hydroxylating long chain hydrocarbons.

Alternatively, commercially available high molecular weight solid carboxylic acids of the formula RCOOH wherein R is a branched chain or linear branched saturated hydrocarbyl radical may be directly used. Such carboxylic acids are sold by Petrolite Polymers Division of Petrolite Corporation as UNICID® carboxylic acids or by New Phase Technologies as PERFORMACID® acids having the formula:

wherein x, R and $R_1$ have the meanings set forth above. A particularly preferred embodiment encompasses the use of UNICID® 350 carboxylic acid.

Liquid oils suitable for use in the invention, especially for external applications include linear or branched chain hydrocarbons, preferably one containing in excess of six carbon atoms, aromatic hydrocarbons as well as cyclic hydrocarbons and petroleum oils. Such hydrocarbons typically may contain up to 60 carbon atoms. Representative hydrocarbons for use in the invention are hexane, octane, n-decane, n-dodecane, n-octadecane, terpenes, paraffin oil, mineral oil, paraffin jelly, iso-paraffins, squalane and squalene; and naturally occurring hydrocarbon mixtures such as petroleum ether and liquid paraffin.

Further, the liquid oils may be selected from a $C_6$ to $C_{18}$ carboxylic acid, such as linoleic acid, oleic acid and capric acid, and triglycerides thereof; esters produced from an aromatic carboxylic acid, typically containing from 5 to 24 carbon atoms, and an; alcohol containing up to 18 carbon atoms; esters produced from a lower fatty acid having between 6 to about 18 carbon atoms, preferably no more than 8 carbon atoms, and an alcohol; silicone oils such as dimethicone; and mixtures thereof.

Especially preferred oils for use in the invention include dimethicone, mineral oil, capric acid, capryl triglyceride and mixtures thereof and a $C_{12}$ to $C_{15}$ alkyl benzoate.

The liquid oils referenced above can be used independently or two or more of them can be used together.

The amount of high molecular weight monocarboxylic acid typically added to the oil-based composition is in the range of about 2 to about 20, preferably up to about 15, most preferably up to about 6, weight percent, based on the total weight of the oil and mnonocarboxylic acid. Typically the higher the concentration of monocarboxylic acid, the thicker the oil based composition. Depending on the oil, solid compositions may typically be reached at concentrations ranging from about 6 to about 15 percent. The molecular weight of the specific monocarboxylic acid may further dictate the amount of monocarboxylic acid to render maximum viscosity of the oil based composition.

The resultant preparation is typically a non-solid, the viscosity dependent on the amount of carboxylic acid added to the oil. Typically, when the amount of monocarboxylic acid is in excess of 15 weight percent, the resulting composition is a solid—the viscosity of the composition increasing with increased concentrations of monocarboxylic acid. Thus, the addition of the carboxylic acid may be controlled to render a gel. Further, the amount of monocarboxylic acid added to the composition is dependent on the identification of the oil. In a preferred embodiment, up to 3.5 weight percent of monocarboxylic acid is used with the oil dimethicone; gel-like solids being produced at a thickening agent concentration of about 3 to about 4 weight percent. Another preferred embodiment contains up to 4% by weight of the monocarboxylic acid with the triglyceride and alkylbenzoate oils. Higher concentrations tend to form solids. For some applications, solids may be the preferred embodiment.

Mineral oil further has been observed to be a highly viscous but pourable liquid at a concentration of monocarboxylic acid of 10 weight percent. At a concentration of 3 to 4, weight percent, the composition is typically of a viscous liquid consistency. With dimethicone, the preferred maximum amount of carboxylic acid to be employed is between 4 and 6 weight percent.

Thus, the viscosity of the desired formulation can be controlled by the selection of the oil as well as by the amount of carboxylic acid added to the oil. For instance, a higher percentage of carboxylic acid may be used when the desired formation is to function as a lipstick versus a moisturizing lotion. Further, a more waxy oil will be desired in the production of a lip gloss or lip balm than in a moisturizing lotion.

The monocarboxylic acid is preferably introduced to the oil-based composition at elevated temperatures. In a preferred embodiment, the molten monocarboxylic acid is mixed with the oil at temperatures at or in excess of the melting point of the monocarboxylic acid. Employing temperatures at less than the melting point of the carboxylic acid typically causes solids to precipitate from the solution. Temperatures should not be so high however to cause decomposition of the oil. During mixing, the long chain carboxylic acid is dissolved into the oil. The admixture is then agitated for a period of time, generally between about two to about four minutes, at an elevated temperature which approximates the melting point of the long chain carboxylic acid. Longer agitation periods typically lead to a breakdown of the oil and further may cause a reaction with the long chain carboxylic acid. Cooling of the mixture renders the desired viscosity of the formulation.

The oil-based composition may further contain a neutralizing agent for the thickening agents. Typically, the neutralizing agent is admixed with the oil prior to the addition of the thickening agent. The amount of neutralizing agent employed typically being no more than that necessary to neutralize the carboxylic acid moiety; in other words the number of equivalents of neutralizing agent may be equal to the number of equivalents of carboxylic acid; typically the resulting composition contains from about 0.5 to about 3.25 weight percent of neutralizing agent. The neutralizing agent may be any conventionally employed in the art, such as triethanolamine (TEA). Neutralized versions yield little, if any, difference in viscosity from unneutralized compositions. The largest difference in the compositions being darker colors in the neutralized compositions resulting from the presence of the TEA.

The oil-based composition to which the solid monocarboxylic acid is added may further contain a hydrophilic or lipophilic material such as those conventionally employed in cosmetic and/or pharmaceutical products. Especially preferred are perfumes, colorants, gelling agents, preservatives, germicides, sunscreens and humectants.

Especially favorable results are obtained when the compositions of the invention are used in the preparation of creams, gels, lotions, and ointments for the cosmetic and pharmaceutical industries. The resulting product will normally be packaged in a convenient dispenser such as a bottle, jar or tube having a closure.

The invention can be used in the production of viscous materials for a variety of purposes including topical applications in the cosmetic and pharmaceutical fields. Such compositions have the ability to cover human or animal skin as well as mucous membranes adjacent the skin; and the mucous membranes in the interior of the body. An advantage of such formulations may be the application as a uniform film.

The invention relates to highly fluid preparations of all consistencies for this purpose, ranging from highly fluid oils of low viscosity, up to creams, salves, emulsions and gels. The latter can be of a nature ranging from fluid oils up to stiff and puncture resistant gels. The compositions of the invention may be formulated into sunscreen and ultraviolet blocking preparations, massage oils, lip ointments as well as ointments and other preparations for medicinal uses.

The method of the invention can be employed in a variety of applications including, in addition to pharmaceuticals and cosmetics, greases and paints. For the preparation of these products, beside liquid oils and gelling agents which are essential for such compositions as lipsticks and lip balms, various optional components can be formulated. Such optional components include, for example, solid oils, purified water, surface active agents (such as those conventionally used for dispersing pigments), humectants, antiseptics, antioxidants, pharmaceutically active components, perfumes and powders. Any such additive conventional in the art may be employed.

The invention has particular applications in thickening dispersions of oil and water. The solid monocarboxylic acid may be added to a vessel containing the oil and these other additives. Alternatively, the monocarboxylic acid may be added to the oil and the composite then mixed with the recited additives.

The amount of solid carboxylic acid used in combination with the oil is between from about 1.0 to about 20% by weight, preferably between from about 2 to about 15% by weight, per the amount of oil.

Desirable formulations of compositions for external application in which the carboxylic acid is added to the oil are as follows:

| Component | Ointment | Cream | Foundation |
|---|---|---|---|
| Carboxylic Acid | 2.5–20 | 0.2–10 | 0.2–10 |
| Liquid Oil | 75–97.5 | 5–80 | 5–80 |
| Pigment | — | — | 2.5–25 |
| Water | 0–40 | 20–95 | 0–50 |
| Other Components (solid, semi-solid oils, etc.) | 0–20 | 0–20 | 0–50 |

The resulting compositions further have an improved appearance and consistency over the compositions of the prior art. While prior art compositions are often clumpy and grainy, the compositions of the invention are smooth. In addition, the compositions of the invention have little, if any, filamentous materials.

Further, the resulting compositions exhibit a high degree of heat stability. As a result, they are capable of being stored for extended periods of time at higher temperatures than the systems of the prior art.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

In the examples, the following components were employed:

Mineral oil—Benol White, a product of Witco Corporation;

Dimethicone—Dimethicone 200 Fluid, 200CST, a product of Dow-Corning;

ABIL EM-90—a water in oil (w/o) emulsifier, composed of Cetyl Dimethicone Copolyol, a product of Goldschmidt Corp.;

Octyl methoxycinnamate—sunscreen of Parsol MCX, a product of Givaudan-Roure, Specialty Div.;

Benzophenone 3—sunscreen of Neoheliopan BB, a product of Haarmann and Reimer;

Preservative—Germaben II-E, a product of Sutton Laboratories;

a $C_{12}$–$C_{15}$ alkyl benzoate—Finsolv TN, a product of Finetex; and

Caprylic/Capric Triglyceride—Crodamol GTC/C.

All percentages expressed herein are percent by weight.

Examples 1–19

A thickening agent was melted in a container. The oil was heated to an elevated temperature in a vessel. The thickening agent was then slowly added to the vessel containing the oil. The mixture was then agitated at high shear in a Lightin' type lab mixer until uniform. The mixture was then removed from heat and mixing and allowed to cool to room temperature. The experimental conditions and the results are set forth in Table I. The results are observed at room temperature.

TABLE I

| EX. NO. | THICKENING AGENT | CONC. OF THICKENING AGT, WT % IN PRODUCED COMPOSITION | OIL | APPROX. TEMP. OF OIL, °F. | AGITATION TIME/MIN | RESULTS |
|---|---|---|---|---|---|---|
| 1 | UNICID ® 700 | 10% (10 g) | Mineral oil | 240 | 10 | Gel at 150° |
| 2 | UNICID ® 350 | 2 g | Mineral oil | 200 | 10–15 | Thickened |
| 3 | UNICID ® 350 | 4 g | Mineral oil | 190 | 2 | Viscous |
| 4 | UNICID ® 350 | 6% | Mineral oil | 200 | 10 | Viscous and thickened at 95° F. |
| 5 | UNICID ® 350 | 10% | Mineral Oil | 212 | 10 | Thickens at 95° F.; smooth gel; pourable |
| 5a | UNICID ® 350 | 0 | Mineral Oil | 72 | — | — |
| 6 | UNICID ® 350 | 15% | Mineral oil | 200 | 15–20 | Gel-like; solid |
| 7 | UNICID ® 350 | 2% | Dimethicone | 190 | 10 | Homogenous, viscous material |
| 7a | UNICID ® 350 | 0% | Dimethicone | 72 | — | — |
| 7b | UNICID ® 350 | 1.5% | Dimethicone | 190 | 10 | Homogenous, viscous material |
| 8 | UNICID ® 350 | 2.5 | Dimethicone | 190 | 2 | Viscous |
| 9 | UNICID ® 350 | 3% | Dimethicone | 190 | 10 | Homogenous, gel-like solid |
| 10 | UNICID ® 350 | 4% | Dimethicone | 190 | 10 | Gel-like solid |
| 11 | UNICID ® 350 | 6% | Dimethicone | 190 | 10 | Homogenous, gel-like solid |
| 12 | UNICID ® 350 | 10% | Dimethicone | 190 | 10 | Gel-like solid, homogenous |
| 13 | UNICID ® 350 | 10% | Triglyceride | 190 | 2 | Gel-like solid |
| 13a | UNICID ® 350 | 0% | Triglyceride | 72 | — | — |
| 14 | UNICID ® 350 | 2.0 | Triglyceride | 190 | 2 | Viscous liquid |
| 14a | UNICID ® 350 | 1.5 | Triglyceride | 190 | 2 | Viscous liquid |
| 15 | UNICID ® 350 | 4% | Triglyceride | 190 | 2 | Gel-like solid |
| 16 | UNICID ® 350 | 6 | Triglyceride | 190 | 2 | Gel-like solid; Harder than 4% |
| 17 | UNICID ® 350 | 2 | Finsolv TN | 190 | 2 | viscous liquid |
| 17a | UNICID ® 350 | 1.5 | Finsolv TM | 190 | 2 | Viscous liquid |
| 18 | UNICID ® 350 | 4 | Finsolv TN | 190 | 2 | Gel-like solid |
| 18a | UNICID ® 350 | 0 | Finsolv TN | 72 | — | — |
| 19 | UNICID ® 350 | 6 | Finsolv TN | 190 | 2 | Gel-like solid; Harder than 4% |
| 19a | UNICID ® 350 | 10 | Finsolv TN | 190 | 2 | Gel-like solid |

Viscosity parameters for selected Examples are further provided in Table II.

TABLE II

| EX. NO. | SPINDLE | RPM | TIME/MINUTES | TEMP. °F. | VISCOSITY, CP |
|---|---|---|---|---|---|
| 2 | 34 | 60 | 10 | 72 | 70.1 |
| 3 | 34 | 60 | 10 | 72 | 556 |
| 4 | 34 | 60 | 10 | 72 | 630 |
| 5a | 31 | 60 | 10 | 72 | 21 |
| 7 | 31 | 30 | 10 | 72 | 641 |
| 7a | 31 | 60 | 10 | 72 | 220 |
| 7b | 31 | 30 | 10 | 72 | 605 |
| 8 | 31 | 3 | 10 | 72 | 4210 |
| 13a | 31 | 60 | 10 | 72 | 27.6 |
| 15 | 34 | 60 | 10 | 77 | 1070 |
| 14 | 34 | 60 | 10 | 77 | 307 |
| 14a | 31 | 60 | 10 | 72 | 185 |
| 17 | 34 | 60 | 10 | 72 | 152 |
| 17a | 31 | 60 | 10 | 72 | 55.9 |
| 18 | 25 | 60 | 10 | 72 | 775 |
| 18a | 31 | 60 | 10 | 72 | 21.5 |

Figure 1:
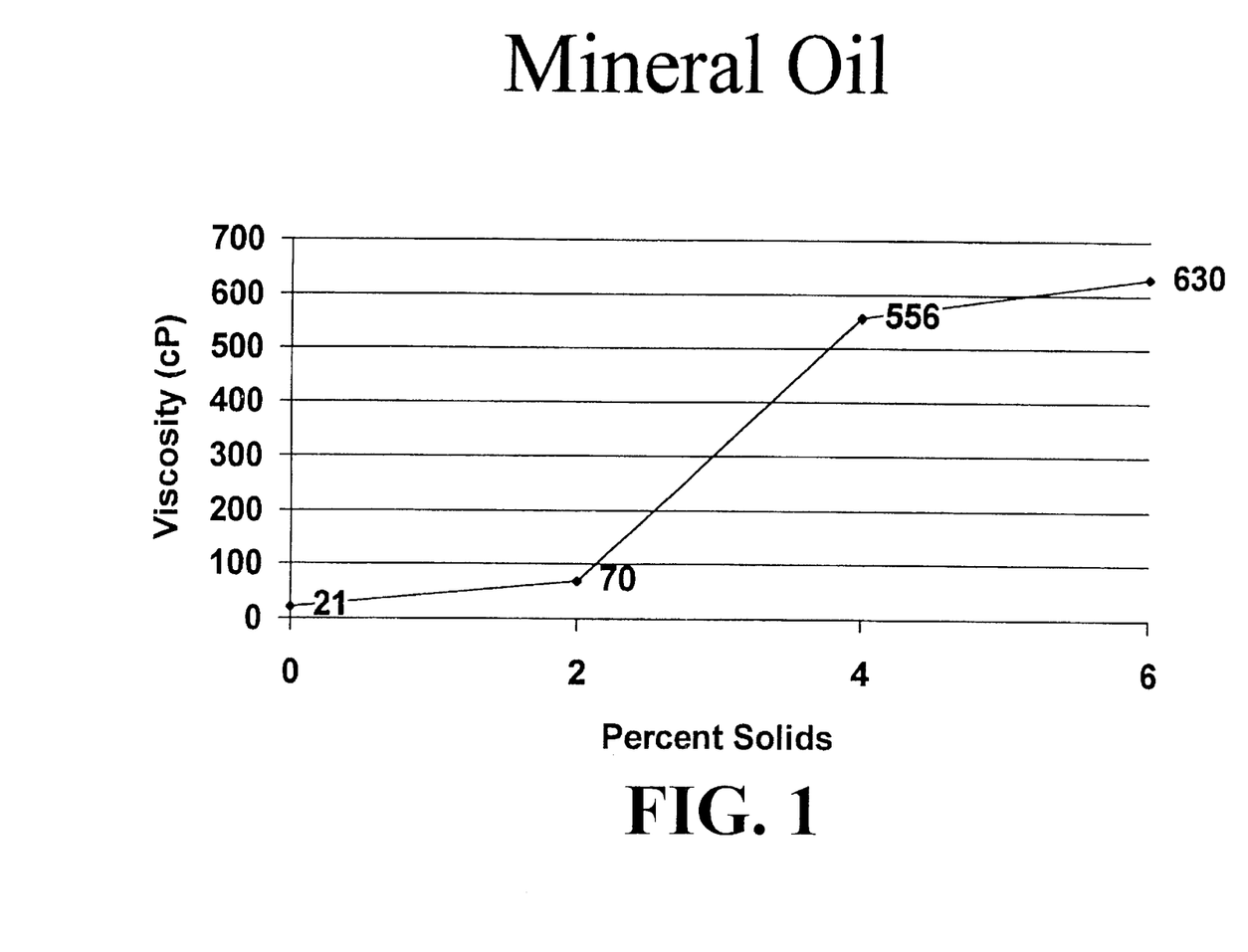
FIG. 1 illustrates the change in viscosity in mineral oil upon the addition of a long chain carboxylic acid in accordance with the invention.
Figure 2:
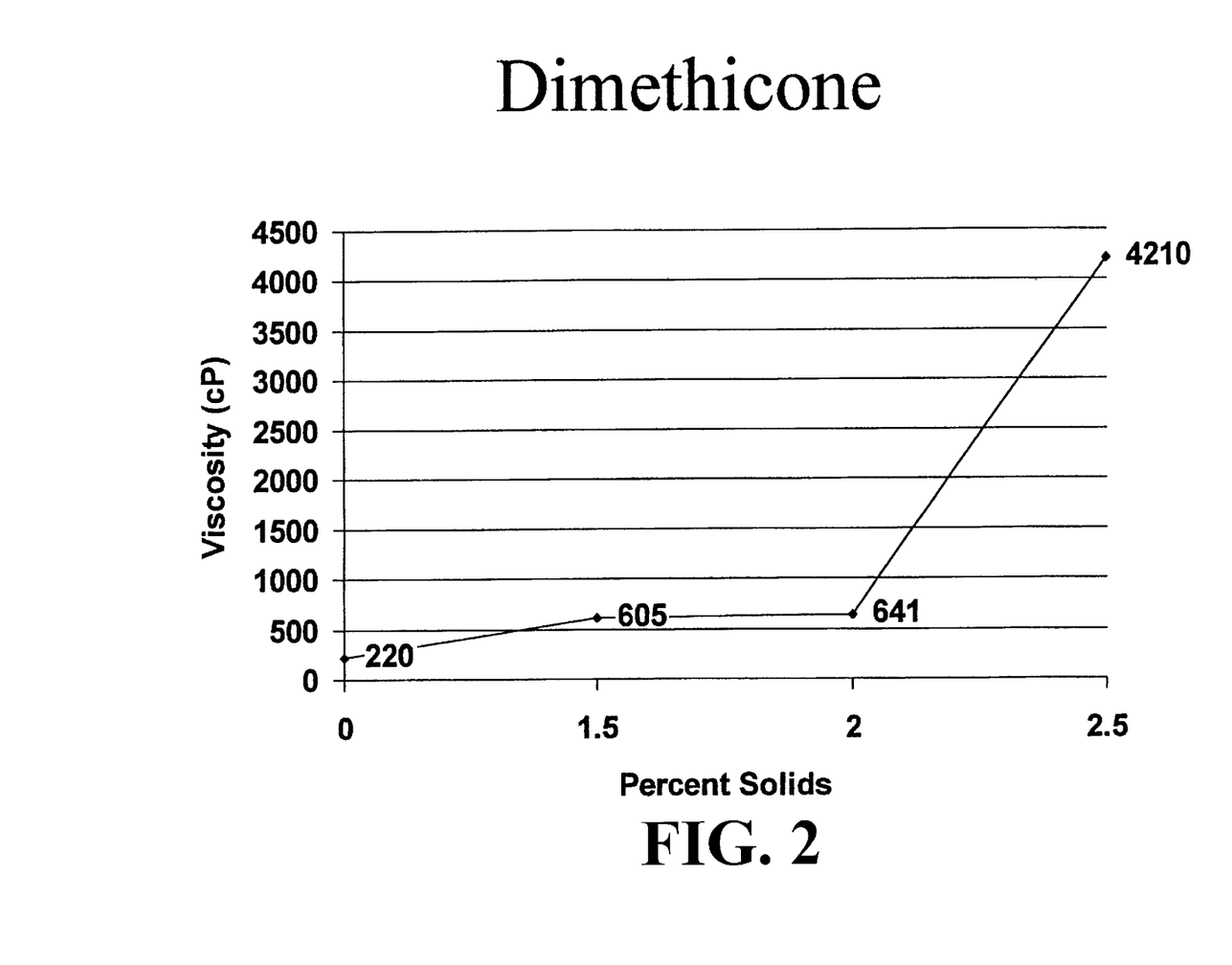
FIG. 2 illustrates the change in viscosity in dimethicone upon the addition of a long chain carboxylic acid in accordance with the invention.
Figure 3:
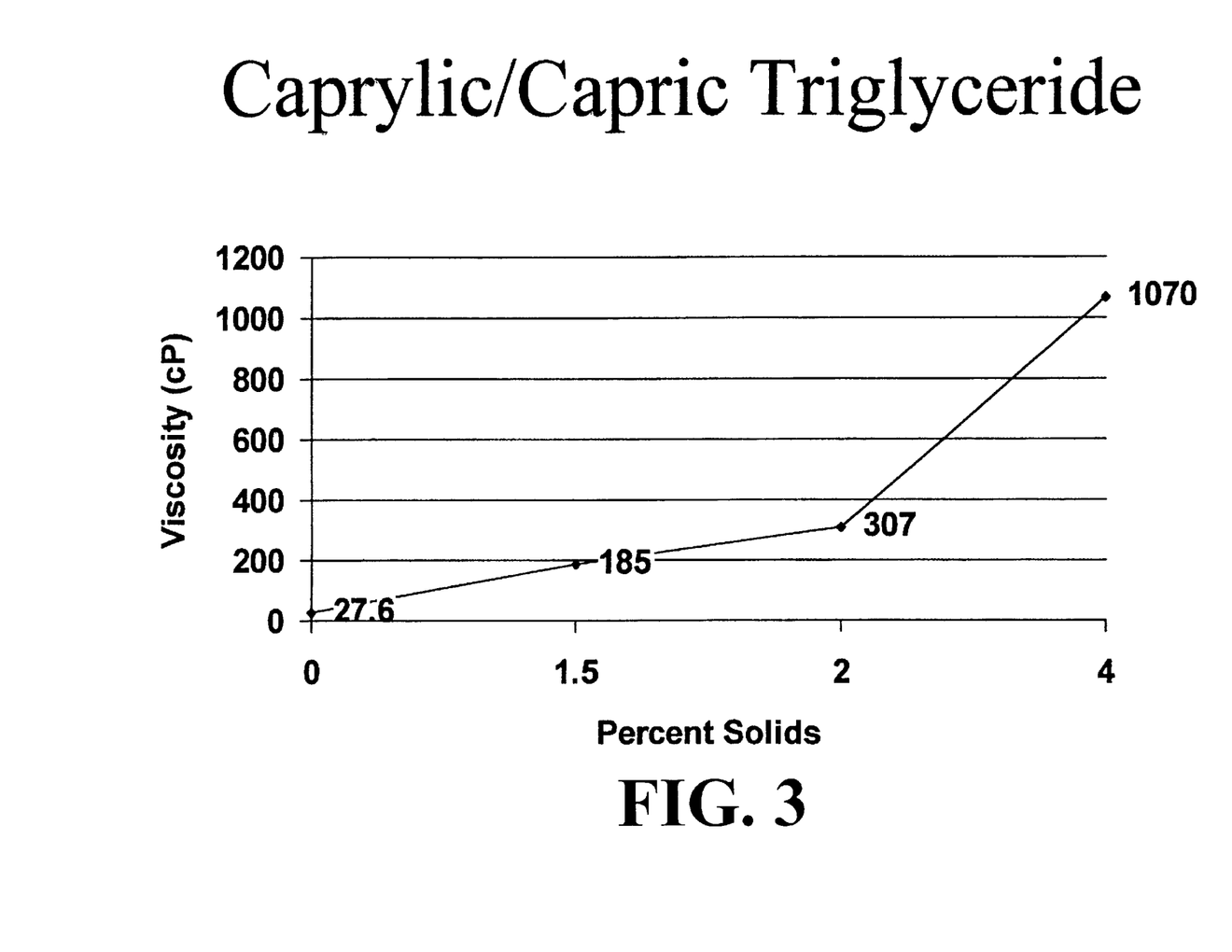
FIG. 3 illustrates the change in viscosity in caprylic/capric triglyceride upon the addition of a long chain carboxylic acid in accordance with the invention.
Figure 4:
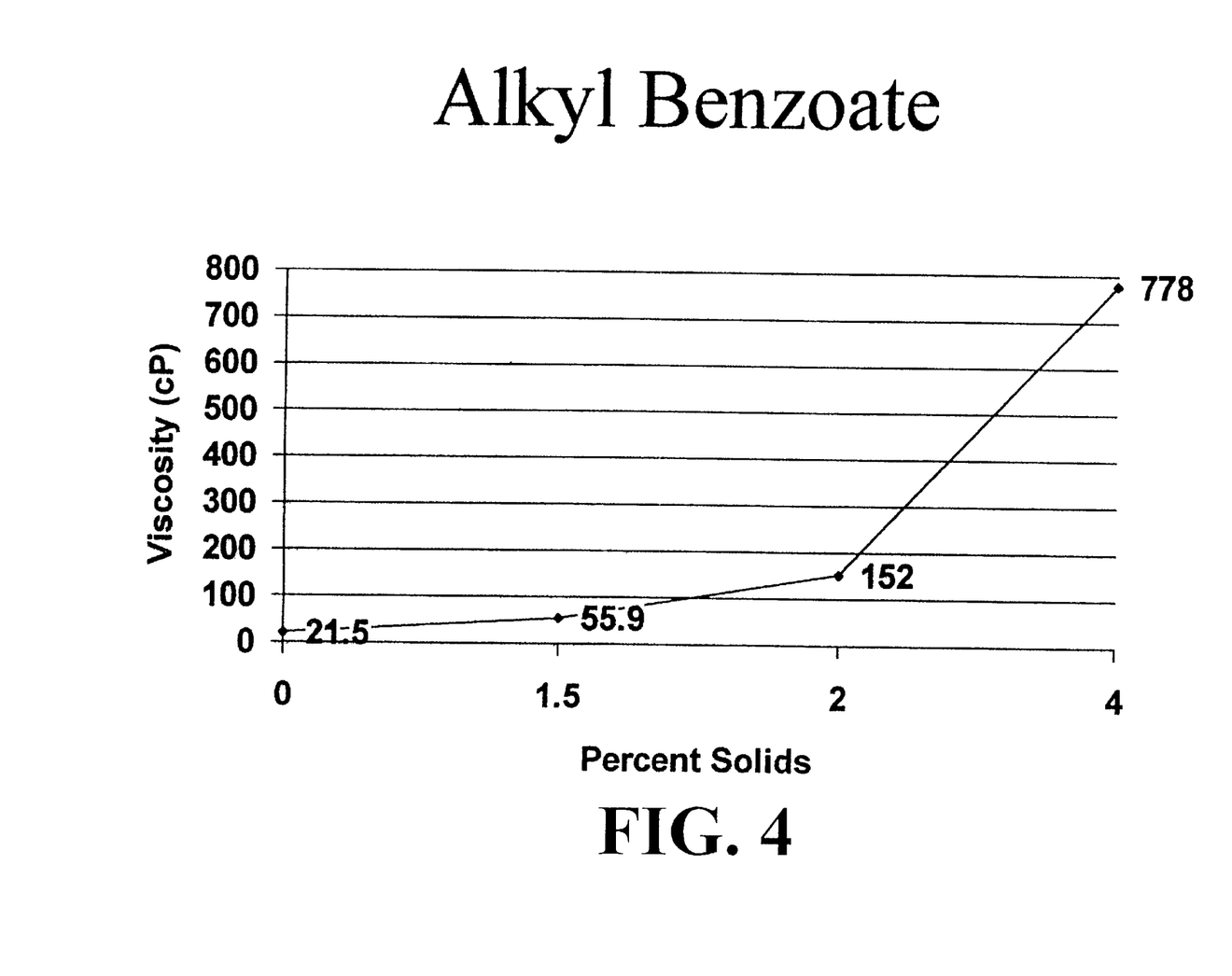
FIG. 4 illustrates the change in viscosity in alkyl benzoate upon the addition of a long chain carboxylic acid in accordance with the invention.

Thickening agents having a molecular weight in excess of 300 were good viscosity enhancers, especially when employed at low concentrations. FIGS. I, II, III and IV illustrate the roughly linear relationship established between increasing concentrations of carboxylic acid and percent solids in the oil-based composition.

Comparative Examples 20–32

The procedures set forth above for Examples 1–19 were repeated. Experimental conditions and results are tabulated in Table III below:

TABLE III

| EX. NO. | THICKENING AGENT | CONC. OF THICKENING AGT, WT % IN PRODUCED COMPOSITION | OIL | APPROX. TEMP. OF OIL, °F. | AGITATION TIME/MIN | RESULTS |
|---|---|---|---|---|---|---|
| 20 | Stearic acid | 6 | Mineral Oil | 195 | 10 | Not viscous/separated |
| 21 | Stearic acid | 10 | Mineral Oil | 195 | 10 | Thickens at 80° F.; |

TABLE III-continued

| EX. NO. | THICKENING AGENT | CONC. OF THICKENING AGT, WT % IN PRODUCED COMPOSITION | OIL | APPROX. TEMP. OF OIL, °F. | AGITATION TIME/MIN | RESULTS |
|---|---|---|---|---|---|---|
| 22 | Stearic acid | 20 | Mineral oil | 195 | 10 | viscous/separated Gel-like |
| 23 | UNICID ® 350 | 2 | Castor Oil | 200 | 10–15 | Little Thickening-homogenous |
| 24 | UNICID ® 350 | 10 | Castor oil | 200 | 10–15 | Dispersion separates |
| 25 | UNICID ® 350 | 6 | Castor oil | 190 | 10–15 | No gel at room temperature |
| 26 | Stearic acid | 2 | Dimethicone | 190 | 10 | Not thick-not homogenous |
| 27 | Stearic acid | 3 | Dimethicone | 190 | 10 | Not homogenous-not viscous |
| 28 | Unicid ® 350 | 10 | Isopropyl myristate | 190 | 10 | Gel-like solid; homogenous |
| 29 | Unicid ® 350 | 2 | Isopropyl myristate | 190 | 10 | No Enhancement |
| 30 | Stearic acid | 2 | Finsolv TN | 150 | 2 | Not viscous/separated |
| 31 | Stearic acid | 6 | Finsolv TN | 150 | 2 | Not viscous/separated |
| 32 | Stearic acid | 2 | Triglyceride | 150 | 2 | Not viscous/separated |

Castor oil and isopropyl myristate were incompatible with the thickening agent. Stearic acid, further, was not compatible with all of the oils tested.

Example Nos. 33–40

Triethanolamine was added to the oil under heat and agitation. In a separate vessel, UNICID® 350 (PERFORMACID® 350 could alternatively be used) was melted at a temperature of approximately 195° F. The UNICID® 350 was then added to the vessel containing the mineral oil and triethanolamine and agitated. The composition was then either quickly cooled or poured directly into a containing jar. The conditions and results are set forth in Table IV.

between 300 and 3,000 exhibited smoother products with less clumpy materials. In addition, such compositions were able to withstand high temperatures. Thus these compositions exhibit longer shelf lives and are able to be shipped at more harsh conditions.

Example No. 41

The stability of some of the compositions were tested. Each of the dispersion samples were placed in an oven at 48° C. Visual results were recorded at the end of the first, second and fourth weeks. The compositions were then shaken back into solution. The first day after shaking, all of the mineral oil, triglyceride and alkyl benzoate samples were stable. The dimethicone containing samples showed some separation

TABLE IV

| EX. NO. | CONC. OF THICKENING AGENT, g | [TEA], g | OIL | [OIL]: g | APPROX. TEMP. OF OIL, °F. | AGITATION TIME/MIN | QUICK COOL | RESULTS | pH OIL/TEA |
|---|---|---|---|---|---|---|---|---|---|
| 33 | 10 | 3.06 | Mineral oil | 86.94 | 200 | 10–15 | Yes | Viscous; more viscous than Ex. 5 | 7.83 |
| 34 | 6 | 1.8 | Mineral oil | 92.2 | 200 | 10–15 | No | Viscous | 7.6 |
| 35 | 2 | 0.61 | Mineral oil | 97.39 | 200 | 10–15 | No | Cloudy | 7.8 |
| 36 | 1 | 0.305 | Finsolv TN | 48.7 | 190 | 2 | No | More viscous than Finsolv TN alone | — |
| 37 | 2 | 0.61 | Finsolv TN | 47.4 | 190 | 2 | No | Viscous gel | — |
| 38 | 6 | 0.916 | Finsolv TN | 46.1 | 190 | 2 | No | Gel-like solid | — |
| 39 | 10 | 1.53 | Finsolv TN | 43.5 | 190 | 2 | No | Gel-like solid; harder than Ex. 38 | — |
| 40 | 1.5 | 0.46 | Triglyceride | 23 | 190 | 2 | No | White-gel; similar to Ex. 16 | — |

Neutralized dispersions demonstrated enhanced viscosity measurements with increased concentration of carboxylic acid.

It was generally observed that the higher molecular weight carboxylic acids render better thickening capabilities at lower concentrations. However, higher molecular carboxylic acids also rendered less smooth compositions. Such compositions typically had pockets of higher viscosities and bumpy areas. Viscous materials and gel-like solids made with monocarboxylic acids having a molecular weight with Example Nos. 11 and 12. Visual results were then recorded for Example 5. Results are tabulated in Table V.

TABLE V

| PRODUCT NO. | FIRST WEEK | SECOND WEEK | FOURTH WEEK | 5 DAYS AFTER SHAKING | 8 DAYS AFTER SHAKING |
|---|---|---|---|---|---|
| 3 | Not observed | Not observed | Separation | High separation | Highest separation |
| 4 | Not observed | Not observed | Separation | Medium separation | High separation |
| 5 | Slight separation at top | Slight separation at top | Separation | Slight separation | High separation |
| 10 | Homogenous | Homogenous | Separation | Slight separation at top | Separation at top |
| 11 | Slight separation at top | Slight separation at top | Separation | Slight separation at top | Separation at top |
| 12 | Slight separation at top | Slight separation at top | Separation | Slight separation at top | Separation at top |
| 13 | Homogenous | No separation | Slight separation at top | Slight separation | Separation at top |
| 15 | Homogenous | No separation | Slight separation at top | Stable | Stable |
| 16 | Homogenous | No separation | Slight separation at top | Stable | Stable |
| 18 | Homogenous | No separation | Slight separation | Stable | Stable |
| 19 | Homogenous | No separation | Separation | Stable | Stable |
| 20 | Homogenous | Homogenous | Separation | Stable | Stable |

The compositions showing separation were then removed from the oven and permitted to sit for one week at room temperature. Example 5 was a gel-like solid, at the end of this period, and had no separation. Examples 3 and 4 were viscous liquids with slight separation at the top. Example 13 was a gel-like solid and had no separation. Examples 10, 11 and 12 were all gel-like solids; Example 12 being harder than Examples 10 and 11. All of samples were stable.

All of the samples were then returned to the oven. Visual observations were then made 15 days after the initial shaking. After being out of the oven for about 5 minutes, all of the compositions formed stable dispersions. Those compositions which could be tested for viscosity were done so on Brookfield DV II, Spindle—25, rpm; 60, temp. 78° F.; time: 10 minutes. The results are tabulated in Table VI

TABLE VI

| EX. NO. | VISCOSITY, CP |
|---|---|
| 3 | 88.2 |
| 4 | 257.0 |
| 5 | Solid |
| 10 | 556 |
| 11 | 982 |
| 12 | Solid |
| 13 | Solid |
| 15 | Solid |
| 16 | Solid |
| 18 | 224 |
| 19 | Solid |

Example No. 42

Ten grams of UNICID® 700 was heated to approximately 230° F. (Alternatively, PERFORMACID® 700 could be employed). The molten carboxylic added was then slowly added to 90 grams of a heated mineral oil maintained at a temperature of approximately 240° F. The mixture was homogenized for approximately ten minutes. The heat was removed and the mixture quickly cooled to 150° F. A gelled solution formed.

Example No. 43

A hand cream was prepared comprised of the following components:

| COMPONENT | % WEIGHT |
|---|---|
| Part A: | |
| Mineral Oil | 10.00 |
| Dimethicone | 7.00 |
| Octyl methoxycinnamate | 5.00 |
| Benzophenone 3 | 2.00 |
| ABIL EM-90 | 1.75 |
| UNICID 350 (or PERFORMACID ® 350) | 2.50 |
| Part B: | |
| Water | 70.45 |
| NaCl | 0.50 |
| Part C: | |
| Preservative | 0.80 |

The hand cream was prepared by heating the components of Part A in a vessel to 190° F. until all parts are melted. The components of Part B are then heated to 180° F. and slowly added to the vessel with proper mixing using a homogenizer, such as the Gifford-Wood Homomixer. The batch was then cooled to 100° F. and Part C—the preservative—was then added. The components were then mixed until a temperature between 75–80° F. was attained. It was then removed from the homogenizer. The hand cream exhibited a viscosity of 400,000 on Brookfield LVT TE at 1.5 rpm.

13

Example No. 44

A cosmetic preparation may be prepared from the following components:

| COMPONENT | % WEIGHT |
|---|---|
| Part A: | |
| Mineral Oil/UNICID 350 (or PERFORMACID ® 350) | 12.50 |
| Part B: | |
| Dimethicone | 7.00 |
| Octyl methoxycinnamate | 5.00 |
| Benzophenone 3 | 2.00 |
| ABIL EM-90 | 1.75 |
| Part C: | |
| Water | 70.45 |
| NaCl | 0.50 |
| Part D: | |
| Preservative | 0.8 |

Part A may consist of 80% mineral oil and 20% UNICID 350 and all the components of Part A may be heated to 190° F. in a vessel. In a separate vessel, are added the components of Part B. These components may then be heated to 190° F. until melted. Part B is then added to the vessel containing Part A with good mixing using a homogenizer, such as the Gifford-Wood Homomixer. Part C, which may first be heated to 180° F., is then slowly added to the vessel with proper mixing. The admixture is cooled to 100° F. and then the preservative of Part D may then be added. Mixing is continued until a temperature of 75–80° F. is attained.

Example No. 45

Ten grams of UNICID® 350 (or PERFORMACID® 350) as heated to approximately 220° F. The molten carboxylic added was then slowly added to 90 grams of a heated mineral oil maintained at a temperature of approximately 200° F. The mixture was agitated for approximately ten minutes. The mixture did not thicken until the temperature was cooled to approximately 95° F. A gelled solution formed.

From the foregoing, it will be observed that numerous variations and modifications may be effected without departing from the true spirit and scope of the novel concepts of the invention.

What is claimed is:

1. A composition for topical application to skin and mucous membranes adjacent the skin, said composition containing:
   (A.) an oil selected from the group consisting of linear and branched chain hydrocarbons, cyclic hydrocarbons, aromatic hydrocarbons, naturally occurring hydrocarbon mixtures, a $C_6$ to $C_{18}$ carboxylic acid and triglycerides thereof, esters of an aromatic carboxylic acid and a $C_6$ to $C_{18}$ alcohol, esters of a lower fatty acid and an alcohol, silicone compounds and mixtures thereof; and
   (B.) a rheologically effective amount of a solid monocarboxylic acid having a number average molecular weight between about 300 and about 3,000.

2. The composition of claim 1 wherein the composition is a liquid.

3. The composition of claim 2, wherein the number average molecular weight of the monocarboxylic acid is less than 2,000.

4. The composition of claim 3, wherein the number average molecular weight of the monocarboxylic acid is less than about 800.

5. The composition of claim 1, wherein the monocarboxylic acid is of the formula RCOOH wherein R is a straight chain saturated hydrocarbyl radical.

6. The composition of claim 1, wherein the monocarboxylic acid is of the formula:

wherein R and $R_1$ independently represent hydrogen or a lower alkyl group of from 1 to about 10 carbon atoms and x represents a number of from about 8 to about 142.

7. The composition of claim 1, wherein the composition is a pourable liquid or a gel or has the consistency of a cream.

8. The composition of claim 6, wherein x is from about 8 to about 112.

9. The composition of claim 1, wherein the oil is selected from the group consisting of mineral oil, silicone oil, caprylic acid, capric triglyceride, a $C_{12}$ to $C_{15}$ alkyl benzoate and mixtures thereof.

10. The composition of claim 9, wherein the silicone oil is dimethicone.

11. The composition of claim 1, wherein the oil is a linear or branched chain hydrocarbon selected from the group consisting of hexane, octane, n-decane, n-dodecane, n-octadecane, terpenes, paraffin oil, paraffin jelly and isoparaffin.

12. The composition of claim 1, wherein the oil is a cyclic hydrocarbon selected from squalane and squalene.

13. The composition of claim 1, wherein the oil is petroleum ether or liquid paraffin.

14. The composition of claim 6, wherein the amount of monocarboxylic acid is from about 2 to about 6 weight percent.

15. The composition of claim 1, wherein the amount of monocarboxylic acid is from about 2 to about 15 weight percent based on the total weight of the composition.

16. The composition of claim 15, wherein the oil is a linear or branched chain hydrocarbon.

17. The composition of claim 16, wherein the linear or branched chain hydrocarbon is mineral oil.

18. The composition of claim 15, wherein the amount of monocarboxylic acid is from about 2 to about 10 weight percent.

19. The composition of claim 18, wherein the amount of monocarboxylic acid is from about 2 to about 10 weight percent and the oil is selected from triglycerides and esters of an aromatic carboxylic acid and a $C_{12}$ to $C_{15}$ alcohol.

20. The composition of claim 18, wherein the amount of monocarboxylic acid is less than 10 weight percent and the oil is a silicone compound.

21. The composition of claim 7, which further contains a perfume, colorant, preservative, germicide, gelling agent, sunscreen or humectant.

22. The composition of claim 1, which further comprises a neutralizing agent.

23. A process of thickening an oil-based composition which comprises adding to said composition a rheologically effective amount of a solid monocarboxylic acid having a number average molecular weight between about 300 and about 3,000, wherein the oil is selected from the group consisting of linear and branched chain hydrocarbons, cyclic hydrocarbons, aromatic hydrocarbons, naturally occurring hydrocarbon mixtures, a $C_6$ to $C_{18}$ carboxylic acid and triglycerides thereof, esters of an aromatic carboxylic acid and a higher alcohol, esters of a lower fatty acid and an alcohol, silicone compounds and mixtures thereof.

24. The process of claim 23, wherein the number average molecular weight of the monocarboxylic acid is less than 2,000.

25. The process of claim 24, wherein the number average molecular weight of the monocarboxylic acid is less than about 800.

26. The process of claim 23, wherein the monocarboxylic acid is of the formula RCOOH wherein R is a straight chain saturated hydrocarbyl radical.

27. The process of claim 23, wherein the oil is selected from the group consisting of mineral oil, dimethicone, a caprylic acid, capric triglyceride, a $C_{12}$ to $C_{15}$ alkyl benzoate and mixtures thereof.

28. The process of claim 23, wherein the oil is a linear or branched hydrocarbon selected from the group consisting of hexane, octane, n-decane, n-dodecane, n-octadecane, terpenes, paraffin oil, mineral oil, paraffin jelly and iso-paraffin.

29. The process of claim 23, wherein the oil is a cyclic hydrocarbon selected from squalane and squalene.

30. The process of claim 23, wherein the oil is petroleum ether or liquid paraffin.

31. The process of claim 23, wherein the oil is a carboxylic acid selected from linoleic acid and oleic acid.

32. The process of claim 23, wherein the amount of monocarboxylic acid in the thickened composition is from about 2 to about 15 weight percent.

33. The process of claim 32, wherein the oil is a mineral oil.

34. The process of claim 32, wherein the amount of monocarboxylic acid in the thickened composition is from about 2 to about 10 weight percent.

35. The process of claim 34, wherein the oil is a triglyceride, an ester of an aromatic carboxylic acid and a $C_{12}$ to $C_{15}$ alcohol or a silicone compound.

36. The process of claim 23, wherein the oil-based composition further contains a perfume, colorant, preservative, germicide, sunscreen or humectant.

37. The process of claim 23, wherein the monocarboxylic acid is of the formula:

wherein R and $R_1$ independently represent hydrogen or a lower alkyl group of from 1 to about 10 carbon atoms and x represents a number of from about 8 to about 142.

38. The process of claim 23, wherein the temperature of the oil-based composition during the addition step is greater than or equal to the melting point of the monocarboxylic acid.

39. The process of claim 23, wherein the oil-based composition to which the monocarboxylic acid is added further contains a neutralizing agent.

40. A method of increasing the viscosity of an oil-based composition which comprises adding a rheologically effective amount of a solid monocarboxylic acid to a liquid composition containing an oil at a temperature in excess of the melting point of the monocarboxlyic acid, wherein the number average molecular weight of the carboxylic acid is between from about 300 to about 3,000.

41. The method of claim 40, wherein the oil is selected from the group consisting of linear and branched chain hydrocarbons, cyclic hydrocarbons, aromatic hydrocarbons naturally occurring hydrocarbon mixtures, a C6 to C18 carboxylic acid, esters of an aromatic carboxylic acid and a higher alcohol, esters of a lower fatty acid and an alcohol, silicone compounds and mixtures thereof.

42. The method of claim 41, wherein the monocarboxylic acid is of the formula:

wherein R and $R_1$ independently represent hydrogen or a lower alkyl group of from 1 to about 10 carbon atoms and x represents a number of from about 8 to about 142.

43. The method of claim 41, wherein the amount of monocarboxylic acid added to the liquid composition is from about 2 to about 15 weight percent of the total weight of the produced composition.

44. The method of claim 43, wherein the amount of monocarboxylic acid added to the liquid composition is from about 2 to about 10 weight percent of the total weight of the produced composition.

45. The method of claim 43, wherein said liquid composition further contains a perfume, colorant, preservative, germicide, sunscreen or humectant.

46. The method of claim 40, wherein the oil-based composition to which is added the monocarboxylic acid further contains a neutralizing agent.

* * * * *